(12) United States Patent
Novak

(10) Patent No.: US 9,962,235 B2
(45) Date of Patent: May 8, 2018

(54) POSITIVE DRIVE CHUCK AND BUR ARRANGEMENT FOR A DENTAL HANDPIECE

(71) Applicant: DENTSPLY INTERNATIONAL INC., York, PA (US)

(72) Inventor: Eugene J. Novak, Deerfield, IL (US)

(73) Assignee: Dentsply Sirona Inc., York, PA (US)

( * ) Notice: Subject to any disclaimer, the term of this patent is extended or adjusted under 35 U.S.C. 154(b) by 0 days. days.

(21) Appl. No.: 14/461,470

(22) Filed: Aug. 18, 2014

(65) Prior Publication Data
US 2014/0356810 A1    Dec. 4, 2014

Related U.S. Application Data

(62) Division of application No. 13/194,285, filed on Jul. 29, 2011.

(51) Int. Cl.
*A61C 1/14* (2006.01)
*A61C 3/02* (2006.01)

(52) U.S. Cl.
CPC .............. *A61C 1/144* (2013.01); *A61C 1/141* (2013.01); *A61C 3/02* (2013.01)

(58) Field of Classification Search
CPC ..... A61C 1/144; A61C 1/141; B23B 31/1078; B23B 31/02
USPC .................................................. 433/127, 129
See application file for complete search history.

(56) References Cited

U.S. PATENT DOCUMENTS

| | | | |
|---|---|---|---|
| 2,801,111 A | 7/1957 | Kaltenbach | |
| 3,082,530 A | 3/1963 | Hopf et al. | |
| 3,175,293 A | 3/1965 | Borden | |
| 3,429,171 A | 2/1969 | Feher | |
| 3,869,796 A | 3/1975 | Thorburn | |
| 4,006,996 A | 2/1977 | Kasabian | |
| 4,290,617 A * | 9/1981 | Yoshida | B23B 31/1071 279/75 |
| 4,509,887 A | 4/1985 | Hofling | |
| 4,571,184 A | 2/1986 | Edwardson | |
| 4,595,363 A | 6/1986 | Nakanishi | |
| 5,040,980 A * | 8/1991 | Heil | A61C 1/141 433/127 |
| 5,275,558 A | 1/1994 | Seney | |

(Continued)

FOREIGN PATENT DOCUMENTS

| | | |
|---|---|---|
| DE | 1119461 | 12/1961 |
| DE | 09210742 | 10/1992 |

*Primary Examiner* — Heidi M Eide
(74) *Attorney, Agent, or Firm* — McNees Wallace & Nurick LLC

(57) ABSTRACT

A chuck assembly for a dental handpiece includes a hollow cylindrical tube portion having a first internal bore, and a chuck portion having a second bore. The chuck portion is supported within the first bore co-rotational with the tube portion about a common axis. The chuck portion has an annular body portion defining the second bore for supporting a cylindrical tool therein. A drive element comprising a drive pin inserted in a first end of the tube portion traverses the first internal bore at a first end of the tube portion. The drive pin cooperates with a distal end of a rotary tool insertable into the second bore to transfer torque to the tool. The tool has an elongated body portion having a driven portion and a working portion. The driven portion includes a shank portion with channels for receiving the drive pin.

10 Claims, 7 Drawing Sheets

(56) References Cited

U.S. PATENT DOCUMENTS

| | | | |
|---|---|---|---|
| 5,549,474 A | | 8/1996 | Cohen |
| 5,924,865 A | | 7/1999 | Quinn |
| 6,155,826 A | * | 12/2000 | Howard ................. 433/129 |
| 6,425,761 B1 | | 7/2002 | Eibofner |
| 7,815,433 B2 | | 10/2010 | Bailey et al. |
| 2003/0163134 A1 | | 8/2003 | Riedel et al. |
| 2006/0281048 A1 | * | 12/2006 | Bailey et al. ............. 433/127 |
| 2009/0220911 A1 | | 9/2009 | Bailey et al. |
| 2009/0325123 A1 | | 12/2009 | Bailey et al. |
| 2010/0221679 A1 | | 9/2010 | Bailey et al. |
| 2011/0129795 A1 | | 6/2011 | Pernot |

* cited by examiner

POSITIVE DRIVE CHUCK AND BUR ARRANGEMENT FOR A DENTAL HANDPIECE

CROSS-REFERENCE TO RELATED APPLICATIONS

This application claims the benefit of, and is a divisional application of co-pending patent application Ser. No. 13/194,285 filed Jun. 29, 2011, entitled "POSITIVE DRIVE CHUCK AND BUR ARRANGEMENT FOR A DENTAL HANDPIECE," which is incorporated herein by reference in its entirety.

FIELD OF THE INVENTION

The present invention relates generally to dental handpieces. More particularly, the present invention relates to a positive drive chuck and bur arrangement for a dental handpiece.

BACKGROUND OF THE INVENTION

Various dental handpieces are known in the dental art. Turbine driven handpieces are widely used by dentists. Dental handpieces include a handle and drive head for supporting the rotating components dental bur. A connector, e.g., a swivel connector, connects the handpiece to various air, water, light and power supply conduits, generally combined in a singular flexible cord. The drive head houses a dental bur drive arrangement that is typically composed of a dental bur-retaining mount or chuck, and a motor or turbine rotatably mounted in the head for driving the chuck. The chuck holds the dental bur for rotation.

The dental bur is removable from the chuck and interchangeable with other dental burs for providing various sizes and dental operations. In known handpieces, the dental bur is maintained by the chuck against axial and radial movement and slippage in the drive arrangement. Screw lock or pushbutton lock arrangements may be provided for the manual locking and releasing of the dental bur in and from the chuck.

Manufacturers of dental handpieces have increased the power wattage that may be output from a dental handpiece. The higher power of the dental handpiece may reduce the percentage of the total power that is delivered to the dental bur. Bur slippage may occur in the chuck during heavy cutting operations, resulting in loss of control of the operation, chatter of the bur during cutting operations, and loss of precision that is essential in dental operations. Slippage of the bur may cause the chuck to wear grooves on the bur shank, causing interference between the bur and the chuck and making removal of the bur from the chuck difficult. Also, unsafe patient conditions may occur due to burs "walking out" of the chuck, i.e., displacing the bur axially out of the chuck due to wear in the chuck.

Further, high frequency or ultrasonic vibrations may cause welding of the bur shank to the chuck. Such unintentional welding requires very high axial applied force to a push button type chuck to release the bur, and may result in chuck or turbine damage, and may require removal of the bur using pliers or forceps.

Prior art chucks of dental handpieces are almost exclusively designed to hold the dental bur by way of friction fit only. Examples of such constructions are found in U.S. Pat. No. 3,869,796, U.S. Pat. No. 4,595,363, U.S. Pat. No. 5,275,558, and U.S. Pat. No. 5,549,474. Only low torque transmission is possible between the chuck and the bur in such constructions, high torque leading to slippage of the bur. At the high rotational speeds achieved and high torque achieved by modern dental handpieces, bur slippage, in both the axial and rotational directions, can become a problem. Rapid deceleration of the bur can also lead to rotational slippage, for example, when the drive continues to rotate while the bur is locked or snagged. Friction between the drive assembly and the dental bur during rotation leads to significant wear of both elements overtime. Friction heat can cause permanent damage to the drive spindle components, especially the flexible friction arms of the chuck, which are normally made of heat tempered material. The damage can lead to rotational slippage and even axial slippage of the dental bur, possibly resulting in an accidental release of the dental bur from the handpiece. Accidental release of a dental bur during high speed rotation can pose a threat to both the patient and the dentist. Continued wear of the bur and drive assembly during operation necessitates routine maintenance and repair of expensive handpiece components.

Thus, a dental handpiece and rotary dental instrument system is desired that reduces slippage and walk out while providing complete power and torque transfer from the dental handpiece and rotary dental instrument and increasing cutting efficiency.

Intended advantages of the disclosed systems and/or methods satisfy one or more of these needs or provide other advantageous features. Other features and advantages will be made apparent from the present specification. The teachings disclosed extend to those embodiments that fall within the scope of the claims, regardless of whether they accomplish one or more of the aforementioned needs.

SUMMARY OF THE INVENTION

It is an object of the present invention to obviate or mitigate at least one disadvantage of prior art handpiece designs.

In a first aspect, the disclosure provides a dental bur for use in a dental bur drive arrangement for a handpiece with a drive head. The rotatable dental bur includes an elongated body portion having a driven portion and a working portion. The driven portion includes a shank portion having at least one channel disposed at a distal end for receiving a drive element of the dental handpiece drive.

In another aspect the disclosure provides a chuck assembly in a dental handpiece that provides positive rotary drive to a dental bur with no slippage, using a cross-pin in a bur tube to cooperate with a groove in the dental bur. The chuck assembly includes a hollow cylindrical tube portion having a first internal bore, and a chuck portion having a second internal bore. The chuck portion is supported within the first internal bore and co-rotational with the tube portion about a common axis. The chuck portion includes an annular body portion defining the second internal bore. The annular body portion retentively supports a cylindrical tool therein. A drive element includes a drive pin inserted in a first end of the tube portion traversing the first internal bore at a first end of the tube portion. The drive pin cooperates with a distal end of a rotary tool insertable into the second internal bore to impart torque to the tool.

In yet another aspect, the disclosure provides a dental handpiece. The dental handpiece includes a handle, a tool-supporting drive head, and a swivel connector for connecting the handpiece to a supply of air, water or electricity. The drive head includes the chuck assembly for a dental handpiece. A hollow cylindrical tube portion having a first internal bore, and a chuck portion having a second internal bore. The chuck portion is supported within the first internal bore and co-rotational with the tube portion about a common axis. The chuck portion includes an annular body portion defining the second internal bore. The annular body portion retentively supports a cylindrical tool therein. A drive element includes a drive pin inserted in a first end of the tube portion traversing the first internal bore at a first end of the tube portion. The drive pin cooperates with a distal end of a rotary tool insertable into the second internal bore to impart torque to the tool.

Other aspects and features of the present invention will become apparent to those ordinarily skilled in the art upon review of the following description of specific embodiments of the invention in conjunction with the accompanying figures.

DETAILED DESCRIPTION OF THE PREFERRED EMBODIMENTS

Dental burs in accordance with the invention are intended for use with a handpiece chuck which is a generally cylindrical member which includes an annular body portion and a plurality of finger springs extending from the body portion, the finger springs are separated by slots, the chuck having a dental bur-receiving axial bore. The finger springs are resiliently deformable and includes a detent or engaging member to interlock with a circumferential groove in the shank or driven portion of the dental bur into the bore. When the dental bur is inserted, detents on finger springs engage a circumferential groove in the shank to retain the dental bur in the bore. A drive pin inserted through a chuck release and bur tube imparts rotational movement to the chuck and the dental bur. The dental bur has a semi-circular groove defined by opposing posts to partially envelop the drive pin when the bur is fully inserted in the bur tube. The chuck further includes a wedge portion for selectively forcing apart the finger springs to release the dental bur. Various dental bur drive arrangements are contemplated in accordance with the present invention, which can allow for torque transfer from the drive directly to the rotatable dental bur.

A rotary positive drive assembly for a dental bur in accordance with the invention includes a rotatable dental bur and a dental bur supporting element for releasably supporting the dental bur. The dental bur supporting element is insertable into a drive head for coaxial rotation in the drive head. The dental bur has a dental bur body having an axis of rotation and is divided into a driven portion, with a driven end for insertion into the dental bur supporting element, and a working portion for projecting from the drive head during use. The dental bur supporting element has a dental bur passage for coaxially receiving the driven portion of the dental bur and supporting it at a predetermined insertion depth.

The invention will now be described in more detail with reference to specific preferred embodiments of the invention directed to an improved dental bur drive arrangement and dental bur, and the dental bur supporting element is a drive spindle, such as a drive spindle for use in a high speed turbine-driven dental handpiece. Although specific reference is made in the following to a dental bur and a drive spindle for a high speed dental handpiece, it will become apparent to those skilled in the art that all structural and functional features of the invention are equally applicable to rotatable dental and medical tools in general and to medical and dental handpieces and other handpieces for supporting high speed rotating tools.

Figure 1:
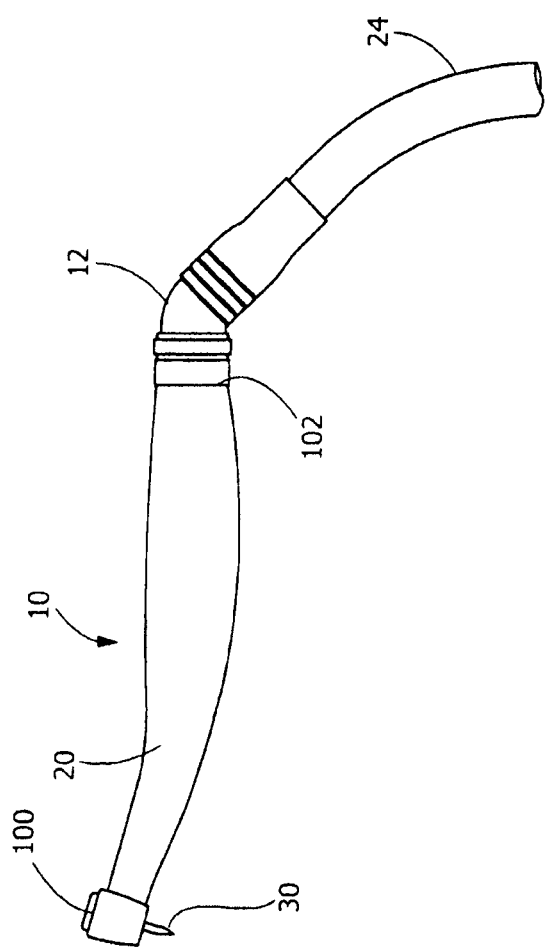
FIG. 1 illustrates an exemplary dental handpiece.

An exemplary dental handpiece 10, as shown in FIG. 1 generally includes a handle 20, a dental bur supporting drive head 100, and a swivel connector 12 for connecting the handpiece to a supply of air, water and in some cases, a supply of electricity. A coupler 102 at the proximal end of the handpiece 10 facilitates the supply of the required resources from the flexible supply connection. The coupler 102 includes seals (not shown), which are typically positioned on its cylindrical portion to isolate water from air and/or electrical power that may be provided. The flexible supply connection 24 typically is a flexible hose that attaches to the coupler 102. The supply connection 24 provides air, water and electricity to handpiece 10 through coupler 102. A flexible supply end is typically affixed to the flexible supply, such as a hose connector using a threaded ring, configured to mate with the coupler supply end, and thus also meets the applicable ISO standard. The coupler may be a swivel coupler that rotates as the handpiece is moved by the dental professional so that the rotational motion of the coupler and flexible supply connection is substantially independent of that of the handpiece, thereby providing the dental professional with some freedom of movement as he/she manipulates the handpiece in the patient's mouth. Drive head 100 receives a dental bur 30, as discussed in greater detail below.

Figure 2:
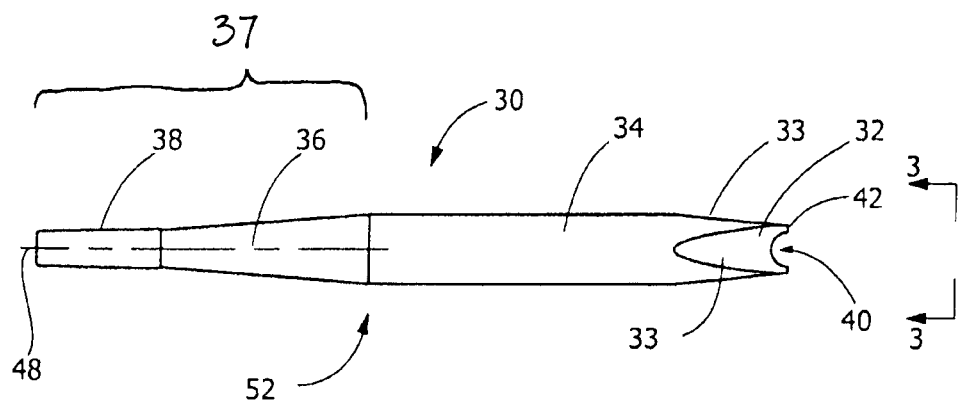
FIGS. 2, 2A, 2B and 2C illustrate various elevational views of a dental bur or rotary tool of the present invention.

Referring to FIG. 2, a dental bur 30 is removably insertable within an internal bore of bur tube 46 (see, e.g., FIG. 4), which is rotatably mounted in drive head 100. In one embodiment, dental bur 30 includes a head portion 32 disposed on a bur shank 34, and a working portion 37 including a transition portion 36, and a tool portion 38. Head portion 32 includes one or more channels 40 defined by opposing walls or posts 42 (see, e.g., FIG. 3). Channels 40 traverse the top of shank portion 34, and channels 40 receive a positive drive pin 72 (see, e.g., FIG. 4). In at least one embodiment, optional tapered flat portions 33 may be used to provide quick alignment between bur channels 40 and drive pin 72. Flat portions 33 are urged into alignment with drive pin 72 by finger springs 56 when inserted into chuck 50.

Figure 2A:
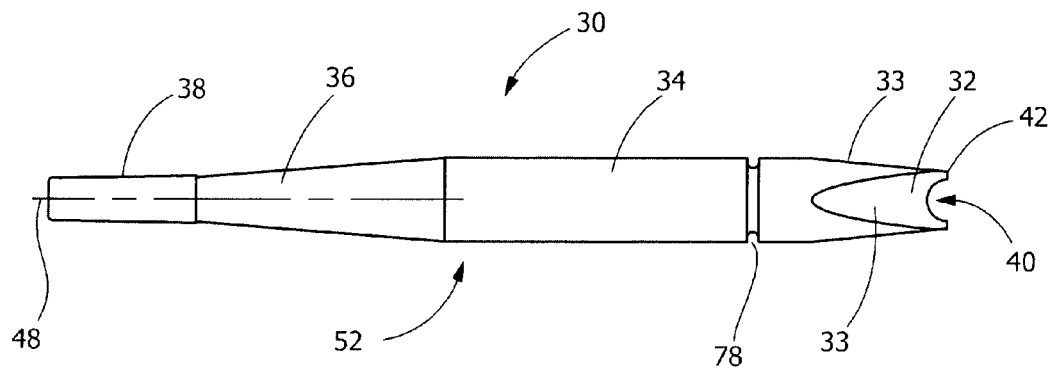
Figure 2B:
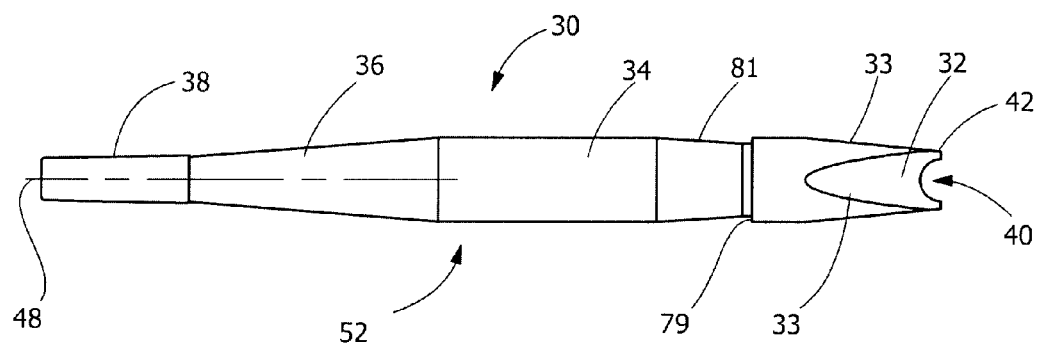
Figure 2C:
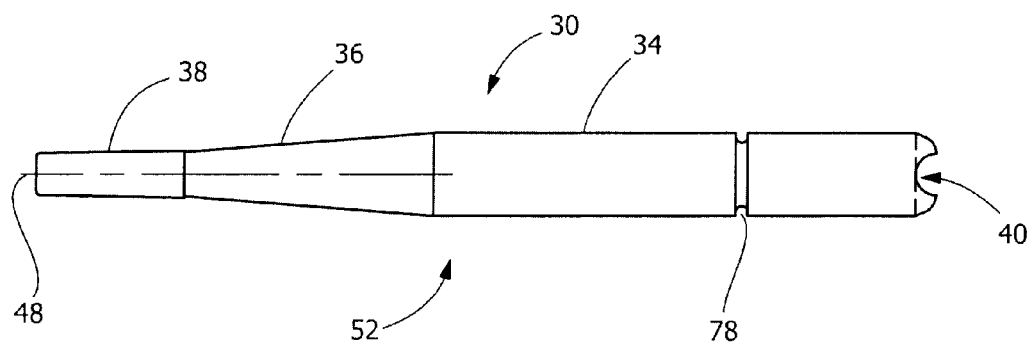

In a preferred embodiment, FIG. 2A shows a dental bur 30 substantially as described in FIG. 2, with an additional feature, a groove 78 for axial positioning of bur 30. Groove 78 interlocks with detents 60 (FIG. 4A) when bur 30 is inserted into chuck 50. In another preferred embodiment, FIG. 2B shows a dental bur 30 substantially as described in FIG. 2, with an additional feature, a shoulder 79 and a tapered surface 81. FIG. 2C shows an example of a dental bur 30 having an optional groove 78, in which the flat portions 33 are omitted and the bur 30 is circular in cross-section throughout.

Figure 4:
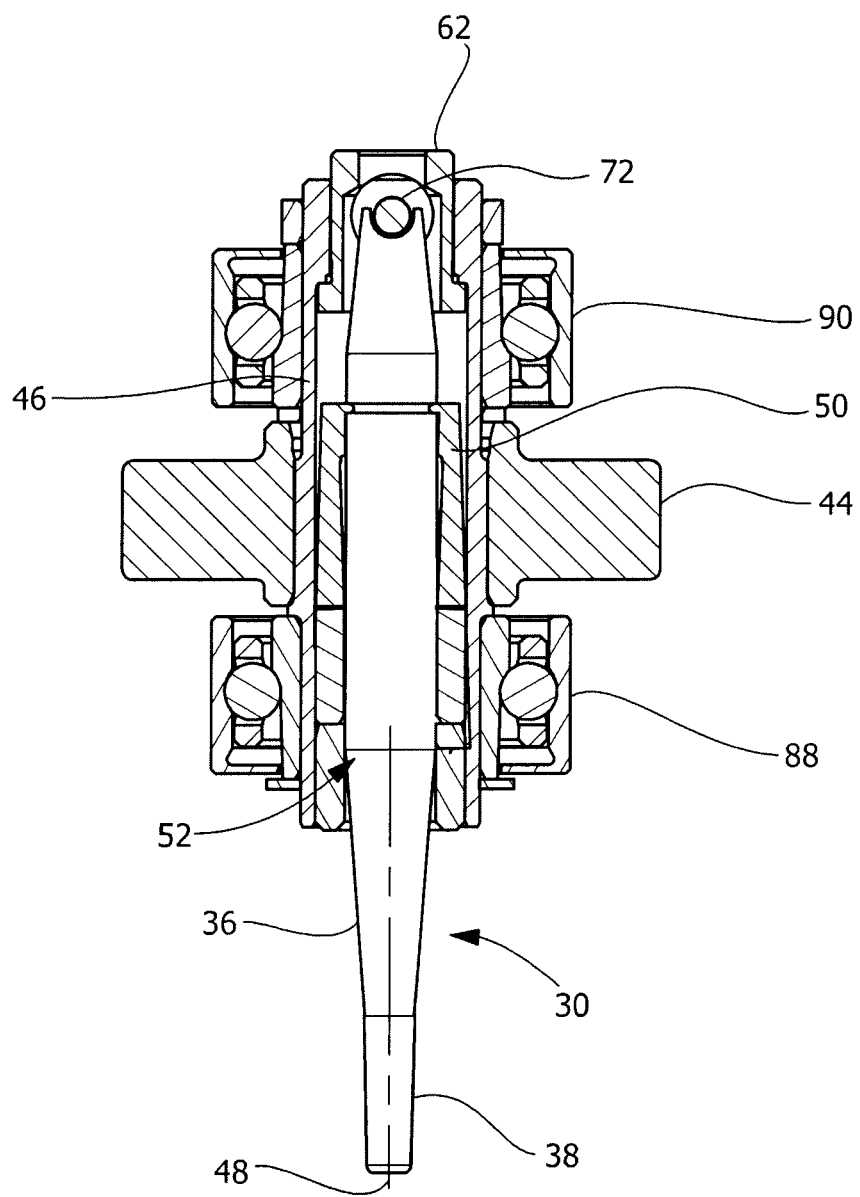
FIG. 4 illustrates a cross-sectional view of a chuck assembly for releasably retaining a dental bur.
Figure 4A:
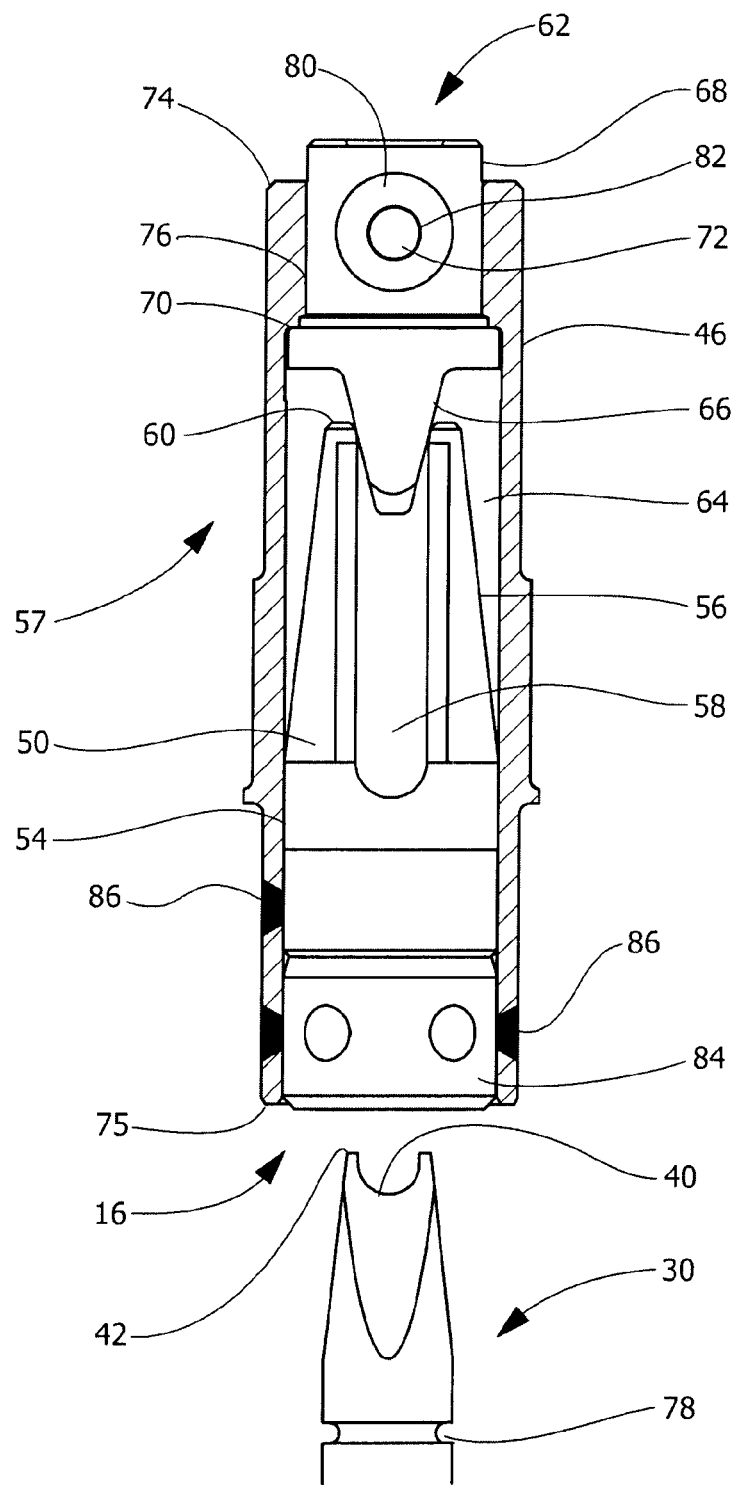
FIG. 4A illustrates another cross-sectional view of the chuck assembly of FIG. 4.

Referring to FIGS. 4 and 4A, drive head 100 includes a torque producing drive 44, typically a motor or turbine rotatably mounted in drive head 100, and having a generally cylindrical, hollow bur tube 46 for housing a chuck 50, arranged to retain dental bur 30 within drive head 100 for rotation about an axis 48. The bur tube 46 and chuck 50 may be retained in the drive head 100 by any means known in the art, e.g., by press-fitting or welding the chuck 50 in the bur tube 46.

Figure 3:
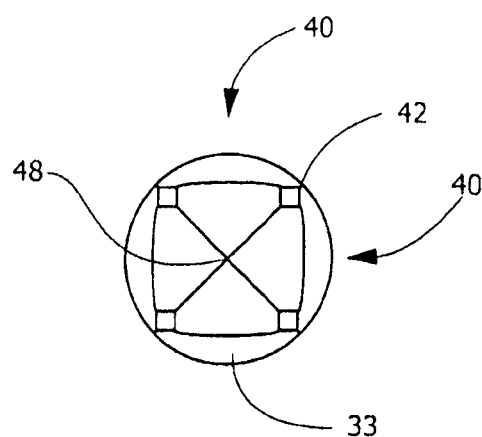
FIG. 3 illustrates an end view of the dental bur in FIG. 2 taken along the lines 3-3.

Referring now to FIGS. 2 and 3, a dental bur such as the dental bur 30 has an elongated body 52 divided into a generally cylindrical shank portion 34 for insertion into the drive head 100 of a dental handpiece 10 for receiving drive torque from the drive head 100 of the handpiece 10, and a transition portion 36 projecting from the drive head 100 of handpiece 10 in an operating condition. The transition portion 36 has a tool portion 38 for engagement with a tooth surface during a dental procedure (not shown). The user, typically a dentist, must purchase a collection of burs varying in length as well as in the structure of the tool portion 38 of the transition portion 36. Bur 30 is generally inserted into the bur tube 46 in the drive head 100 and is removably supported therein by the chuck 50 for rotation with the bur tube 46 about the axis of rotation 48.

As illustrated in FIGS. 4 and 4A, a preferred embodiment of the dental bur drive arrangement includes a chuck 50 for retaining bur 30. Chuck 50 includes an annular body portion 54 and a plurality of finger springs 56 extending from body portion 54. Finger springs 56 are separated by slots 58. Finger springs 56 have detents 60 projecting radially inward from a distal end 57 of finger spring 56 towards axis of rotation 48. In the embodiment shown in FIGS. 4 and 4A, there are two finger springs 56, although three, four or more finger springs may also be used within the scope of the present disclosure. Finger springs 56 are tapered inwardly to provide space 64 within the hollow bore 62 of bur tube 46, and to provide flexibility of finger springs 56 to deflect outwardly when finger springs 56 are impinged upon by wedge portion 66. Wedge portion 66 extends from an annular chuck release element 68. Chuck release element 68 rides or floats in the top of bur tube 46. Finger springs 56 support chuck release element 68 in contact with wedge portion 66. A shoulder portion 70 extends radially outward from chuck release element 68 adjacent wedge portion 66. Shoulder portion 70 cooperates with an inner shoulder portion 76 on bur tube 46 that reduces the internal bore 62 adjacent first end 74 to a diameter that is less than the outside diameter of shoulder portion 70, limiting axial travel of chuck release element 68 in the direction of bur tube end 74.

In a preferred embodiment bur 30 includes an optional detent groove 78 adjacent head portion 32. Groove 78 engages detents 60 on finger springs 56 when bur 30 is inserted into bur tube 46, retaining bur 30 in axial position with respect to bur tube 46. A drive pin 72 traverses through pin aperture 80 extending through chuck release portion 68. Drive pin 72 extends through pin aperture 80 and into the walls of bur tube 46 and engages bur tube 46 frictionally at both ends of drive pin 72. Apertures 82 at diametrically opposite sides of bur tube 46 receive drive pin 72 when in position within bur tube 46 keeping drive pin 72 stationary within bur tube 46. Ring 92 (FIG. 5) retains drive pin 72 in bur tube 46.

When bur 30 is axially inserted into bur tube 46, finger springs 56 flex outwardly at the distal end 57 and apply radial force on detents as groove 78 aligns with detents 60, causing detents 60 to lock into groove 78 and retain the axial position of bur 30. Channel 40 in head portion 32 cooperates with drive pin 72, partially surrounding drive pin 72 so that posts 42 interfere with drive pin 72 when bur tube 46 rotates within head portion 100. Thus, a direct or positive drive rotational force is imparted from bur tube 46 to bur 30 through posts 42. It should be noted again that post 42 may configured around a single groove across head portion 32, rather than, as shown, around a pair of perpendicular intersecting grooves on head portion 32. Drive pin 72 thus prevents any slippage of dental bur 30 relative to bur tube 46.

Bur tube 46 includes a pilot bushing 84, or friction ring, positioned at the second end 75 of bur tube 46. Pilot bushing 84 is adjacent or abutting chuck body 54 within bore 62. Pilot bushing 84 is fixed in position in bur tube 46 by laser welds 86 or other suitable fastener. Pilot bushing 84 allows a standard dental bur—i.e., a dental bur with no grooves 40 or posts 42 formed at the end. Pilot bushing 84 is fixed in the bore opening by laser welds 86 and chuck 50. Pilot bushing 84 has an internal bore 16 with close tolerance fit to dental bur 46, to minimize chatter when the bur is rotating at high speeds. In one embodiment pilot bushing 84 may be made of carbide or other hard material to prevent wear on pilot bushing 84 and chuck 50. A standard dental bur may be inserted into bur tube 46 to the depth defined by the drive pin 72.

A standard bur, when inserted in chuck 50, may abut the drive pin 72, but will not provide the interference necessary for the positive drive of bur 30. Also, a standard dental bur may or may not include a detent groove 78. A standard dental bur without a detent groove 78 will not lock into position axially, but instead relies on friction grip on the standard dental bur to provide the rotational torque, thus requiring a greater gripping force and greater release force to release the bur from the chuck, as is typical in conventional dental handpieces and drives.

With drive pin 72 providing positive drive to bur 30 via channel 40, it is not necessary to rely on chuck 50 to prevent slippage. Also, with detent groove 78 interlocking with detents 60, axial movement of the bur 30 is limited, and chuck 46 may only be a supplemental aid to prevent the bur from "walking out" of bore 62. This configuration for the dental handpiece provides a means to provide a dramatic reduction in the force applied to pushbutton release. Whereas the force required to release a dental bur in a prior art releasable chuck arrangement may range from 10 to 12 pounds force, the disclosed chuck assembly 50 used with dental bur 46 having groove 78 (FIG. 2A) or taper 81 (FIG. 2B) requires only a fraction of the force be applied to chuck release 68 in order to release bur 30, e.g., in a range of 2 to 4 pounds force.

Figure 5:
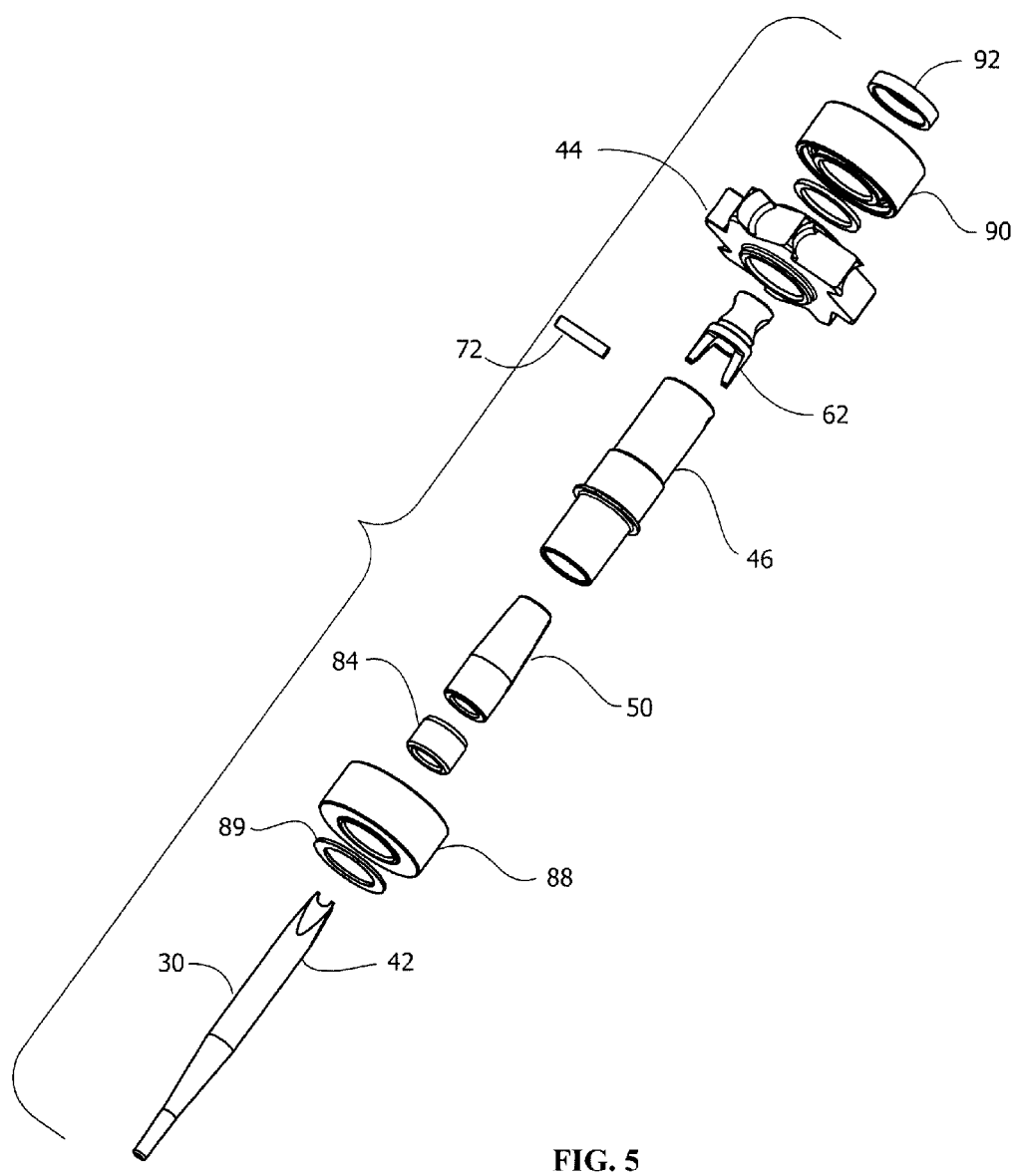
FIG. 5 illustrates an exploded view of the chuck assembly of FIG. 4.
Figure 6:
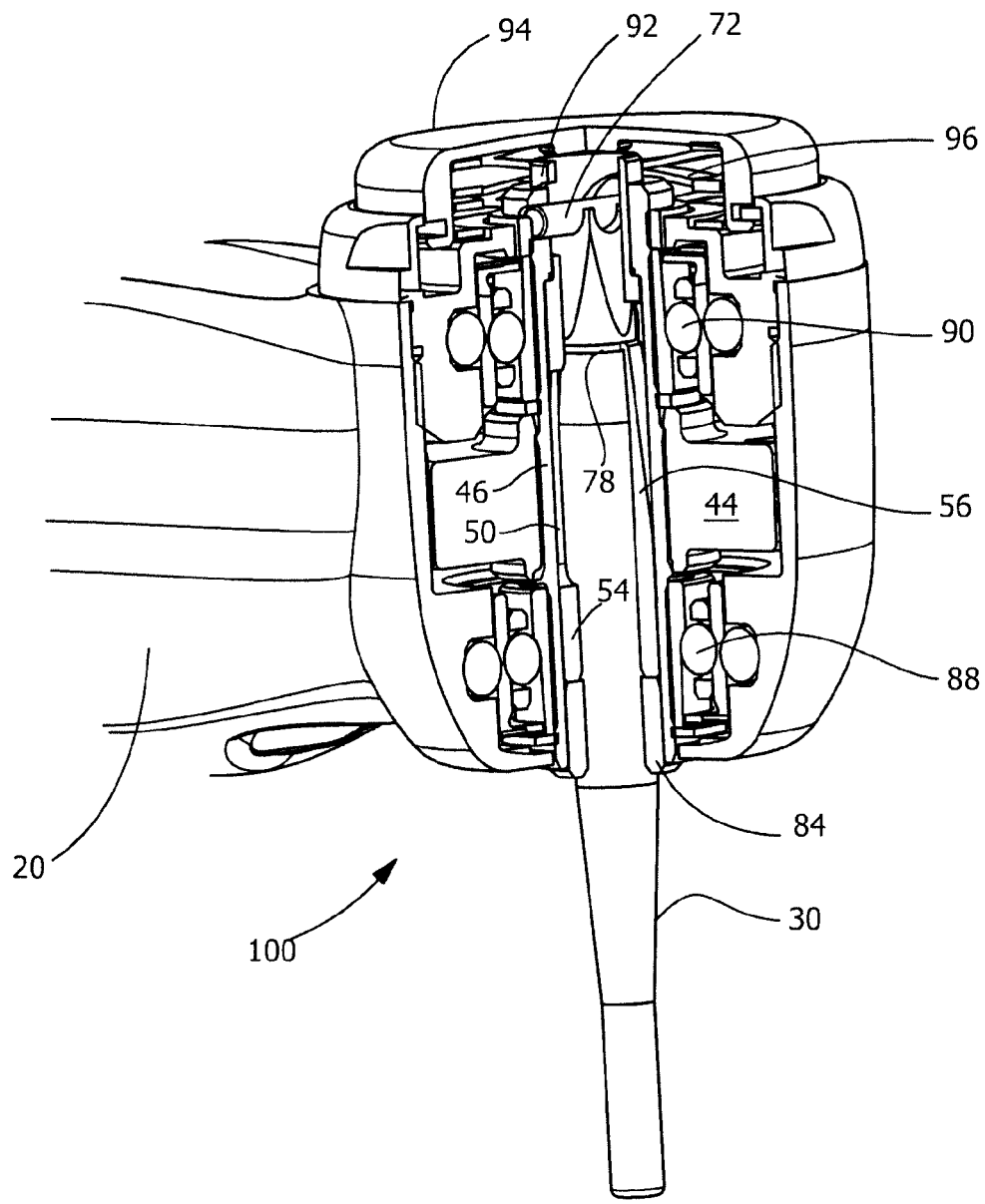
FIG. 6 illustrates a sectional view of an exemplary chuck assembly mounted in a drive head.

Referring next to FIGS. 5 and 6, an exploded view of the dental bur 30 and chuck 50 arrangement is shown. Bur 30 with channel or channels 40 is inserted through ball bearing assembly 88 and seal ring 89 into the bore 62 of chuck 50. Pilot bushing 84 may be an integral part of bearing assembly 88, e.g., providing the inner race portion of a ball bearing assembly 88, or may be positioned adjacent to ball bearing assembly 88. Chuck 50 and chuck release 68 are inserted in opposite ends of bur tube 46, and chuck release 68 coupled with bur tube 46 by cross-pin 72. The length of bur tube 46 from the insertion end to the outer surface of drive pin 72 corresponds with the length of shank portion 34 to approximately the lowest point of channel 40, allowing posts 42 to engage drive pin 72 during rotation of bur tube 46. Bur tube 46 is driven by drive 44, which as discussed above may be, e.g., a pneumatic turbine or an electric motor, or other prime mover. Drive 44 is connected on the outer perimeter of bur tube 46. A second ball bearing assembly 90 rotatably supports bur tube 46 adjacent the second end of bur tube 46.

Referring to FIG. 6, the chuck 50 and bur tube 46 are shown pressed into position within the drive head 100. A pushbutton arrangement 94 when depressed cooperates with chuck release 68 to release bur 30 from bur tube 46 when pushbutton arrangement 92 is depressed. Pushbutton arrangement 92 may include a spring 96, e.g., a leaf spring or coil spring, for retracting the pushbutton arrangement 94 away from bur tube 46 or chuck release during normal operation of handpiece drive head 100.

While the exemplary embodiments illustrated in the figures and described herein are presently preferred, it should be understood that these embodiments are offered by way of example only. Other substitutions, modifications, changes and omissions may be made in the design, operating conditions and arrangement of the exemplary embodiments without departing from the scope of the present application. Accordingly, the present application is not limited to a particular embodiment, but extends to various modifications that nevertheless fall within the scope of the appended claims. It should also be understood that the phraseology and terminology employed herein is for the purpose of description only and should not be regarded as limiting.

It is important to note that the construction and arrangement of the present application as shown in the various exemplary embodiments is illustrative only. Only certain features and embodiments of the invention have been shown and described in the application and many modifications and changes may occur to those skilled in the art (e.g., variations in sizes, dimensions, structures, shapes and proportions of the various elements, values of parameters e.g., temperatures, pressures, etc., mounting arrangements, use of materials, orientations, etc.) without materially departing from the novel teachings and advantages of the subject matter recited in the claims. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. It is, therefore, to be understood that the appended claims are intended to cover all such modifications and changes as fall within the true spirit of the invention. Furthermore, in an effort to provide a concise description of the exemplary embodiments, all features of an actual implementation may not have been described (i.e., those unrelated to the presently contemplated best mode of carrying out the invention, or those unrelated to enabling the claimed invention). It should be appreciated that in the development of any such actual implementation, as in any engineering or design project, numerous implementation specific decisions may be made. Such a development effort might be complex and time consuming, but would nevertheless be a routine undertaking of design, fabrication, and manufacture for those of ordinary skill having the benefit of this disclosure, without undue experimentation.

What is claimed is:

1. A chuck assembly for a dental handpiece, the chuck assembly comprising:
    a hollow cylindrical tube portion having a first internal bore, and a chuck portion having a second internal bore,
    the chuck portion supported within the first internal bore and co-rotational with the tube portion about a common axis;
    the chuck portion comprising an annular body portion defining the second internal bore, for retentively supporting a cylindrical tool capable of being inserted therein but not preventing rotational slippage of the tool about the axis, the annular body portion further comprising a ring portion and a plurality of flexible, elongate springs, the springs separated by slots, the springs extending longitudinally from the ring portion and parallel with the axis, the springs tapering radially inwardly away from an internal surface of the tube portion towards the axis to provide flexibility to deflect outwardly, the plurality of elongate springs further comprising a detent projecting radially inward capable of engaging a shoulder in the tool to axially position and retain the tool within the chuck portion when received therein; and
    a drive element comprising a drive pin inserted in a first end of the tube portion traversing the first internal bore at the first end of the tube portion, the drive pin cooperative with at least one channel disposed at a distal end of the tool capable of being inserted into the second internal bore to impart torque to the tool when inserted therein;
    wherein the detent and the drive pin are capable of engaging the shoulder and the at least one channel, respectively, to axially position and retain the tool within the chuck portion when received therein.

2. The chuck assembly of claim 1, wherein the chuck assembly further includes a release portion disposed within the first internal bore adjacent the chuck portion, the release portion engageable with the chuck portion to displace distal ends of the elongate springs radially outward toward the internal surface of the tube portion a sufficient amount capable of releasing the tool from the second internal bore.

3. The chuck assembly of claim 2, wherein the release portion comprises a wedge portion comprising an aperture for the drive pin to pass through, the wedge portion having a tapered member positioned adjacent the springs and movable within the first bore, wherein when the wedge portion is axially advanced between the springs, the detents capable of disengaging with the channel to release the tool when the tool is present in the second internal bore.

4. The chuck assembly of claim 1, the tool further comprising a rotatable dental bur, the dental bur comprising:
    an elongated body portion having a driven portion and a working portion;
    the driven portion including a shank portion having at least one channel disposed at a distal end for receiving the drive element of a dental handpiece drive.

5. A dental handpiece comprising a handle, a tool-supporting drive head, a swivel connector for connecting the handpiece to a supply of air, water or electricity, the drive head comprising:
    a chuck assembly for a dental handpiece, the chuck comprising:
    a hollow cylindrical tube portion having a first internal bore, and a chuck portion having a second internal bore,
    the chuck portion supported within the first internal bore and co-rotational with the tube portion about a common axis;
    the chuck portion comprising an annular body portion defining the second internal bore, for retentively supporting a cylindrical tool capable of being inserted therein but not preventing rotational slippage of the tool about the axis, the annular body portion further comprising a ring portion and a plurality of flexible, elongate springs, the springs separated by slots, the springs extending longitudinally from the ring portion and parallel with the axis, the springs tapering radially inwardly away from an internal surface of the tube portion towards the axis to provide flexibility to deflect outwardly, the plurality of elongate springs further comprising a detent projecting radially inward capable of engaging a shoulder in the tool to axially position and retain the tool within the chuck portion when received therein; and a drive element comprising a drive pin inserted in a first end of the tube portion traversing the first internal bore at the first end of the tube portion, the drive pin cooperative with at least one channel disposed at a distal end of the tool insertable into the second internal bore to impart torque to the tool;

wherein the detent and the drive element are capable of engaging the shoulder and the at least one channel, respectively, to axially position and retain the tool within the chuck portion when received therein.

6. The dental handpiece of claim 5, the tool further comprising a rotatable dental bur, the dental bur comprising:

an elongated body portion having a driven portion and a working portion;

the driven portion including a shank portion having at least one channel disposed at a distal end for receiving the drive element of a dental handpiece drive.

7. The dental handpiece of claim 5, wherein the chuck assembly further includes a release portion disposed within the first internal bore adjacent the chuck portion, the release portion engageable with the chuck portion to displace distal ends of the elongate springs radially outward towards the internal surface of the tube portion a sufficient amount capable of releasing the tool from the second internal bore.

8. The dental handpiece of claim 7, wherein the release portion comprises a wedge portion comprising an aperture for the drive pin to pass through, the wedge portion having a tapered member positioned adjacent the springs and movable within the first bore, to axially advance the wedge portion between the springs such that the detents disengage with the channel and release the tool when the tool is present in the second internal bore.

9. The dental handpiece of claim 8, wherein the dental handpiece further comprises a push button assembly adjacent the release portion for applying an axial force on the wedge portion.

10. The dental handpiece of claim 9, wherein the push button assembly has a return spring to urge a push button away from a release position.

* * * * *